(12) United States Patent
Avissar et al.

(10) Patent No.: US 7,736,621 B2
(45) Date of Patent: Jun. 15, 2010

(54) METHODS FOR GAUGING THE EFFECT OF A DEPRESSION TREATMENT BY DETERMINING THE LEVELS OF BETA-ARRESTIN 1 AND G-PROTEIN COUPLED RECEPTOR KINASE 2

(75) Inventors: Sofia Avissar, Omer (IL); Gabriel Schreiber, Omer (IL)

(73) Assignee: Hypatia Ltd., Herzalia (IL)

( * ) Notice: Subject to any disclaimer, the term of this patent is extended or adjusted under 35 U.S.C. 154(b) by 509 days.

(21) Appl. No.: 11/195,658

(22) Filed: Aug. 3, 2005

(65) Prior Publication Data

US 2006/0029985 A1 Feb. 9, 2006

(30) Foreign Application Priority Data

Aug. 3, 2004 (IL) .................................. 163332

(51) Int. Cl.
*A61K 49/00* (2006.01)
(52) U.S. Cl. .................. 424/9.2; 436/514; 436/516; 436/518; 424/9.1
(58) Field of Classification Search .................. None
See application file for complete search history.

(56) References Cited

OTHER PUBLICATIONS

Nestler et al. Neuron. 2002 34: 13-25.*
Grange-Midroit et al. Mol Brain Res. 2003, 111: 31-41.*
Avissar et al. Am. J. Psychiatry. Nov. 2004. 161: 2066-2072.*
Avissar et al. Am. J. Psychiatry. 1997. 154: 211-217.*
Bohn et al., NeuroMolecular Medicine. 2004. 5:41-50.*
"Towards Molecular Diagnostics of Mood Disorders In Psychiatry," *Trends in Molecular Medicine*, 8: 294-300, by Sofia Avissar et al., 2002.
"Applications of G Proteins in the Molecular Diagnosis of Psychiatric Disorders," *Expert Review of Molecular Diagnosis*, 3: 89-100, by Sofia Avissar et al., 2003.

* cited by examiner

*Primary Examiner*—Christine J Saoud
*Assistant Examiner*—Chang-Yu Wang
(74) *Attorney, Agent, or Firm*—Baker Botts L.L.P.

(57) ABSTRACT

The invention provides a diagnostic composition for detecting an affective disorder comprising an antibody selected from the group consisting of an antibody to a beta-arrestin, an antibody to a G-protein coupled receptor kinase and combinations thereof as the active detecting agent therein.

8 Claims, 13 Drawing Sheets

Decreased GRK2 levels in the cytosolic fraction of MNLs obtained from patients with depression \* Significant difference between depressed patients and normal subjects ($p<0.05$)

METHODS FOR GAUGING THE EFFECT OF A DEPRESSION TREATMENT BY DETERMINING THE LEVELS OF BETA-ARRESTIN 1 AND G-PROTEIN COUPLED RECEPTOR KINASE 2

BACKGROUND

The present invention relates to a diagnostic composition for detecting an affective disorder, to methods utilizing the same and to kits containing the same. More particularly the present invention relates to compositions, methods and kits for diagnosis and monitoring of treatment of affective disorders.

Mental disorders with their very high prevalence and incidence represent a significant share of all causes of disability worldwide. In 1990, the World Health Organization (WHO) have calculated that of the ten leading causes of disability worldwide four are mental disorders and the number one cause is unipolar major depression (Table 1).

TABLE 1

Leading Causes of Disability Worldwide, World Health Organization 1990

|  | Total (millions) | Percent of total |
|---|---|---|
| 1. Unipolar major depression | 50.8 | 10.7 |
| 2. Iron-deficiency anemia | 22.0 | 4.7 |
| 3. Falls | 22.0 | 4.6 |
| 4. Alcohol use | 15.8 | 3.3 |
| 5. Chronic pulmonary disease | 14.7 | 3.1 |
| 6. Bipolar disorder | 14.1 | 3.0 |
| 7. Congenital anomalies | 13.5 | 2.9 |
| 8. Osteoarthritis | 13.3 | 2.8 |
| 9. Schizophrenia | 12.1 | 2.6 |
| 10. Obsessive-compulsive disorder | 10.2 | 2.2 |
| All causes | 472.7 |  |

Major depression ranked fourth, behind lower respiratory infections, diarrheal diseases, and perinatal conditions, in terms of disease burden measured in disability-adjusted life years. The National Co-morbidity Study, a large scale epidemiological survey of mental illness prevalence, indicated that the life time prevalence of major depression is 17%. The survey also indicated that in any given year 10% of the individuals, aged 18-54 years, suffer from a depressive disorder.

Most of the present modalities of pharmacological treatments in mental disorders already exist for about 50 years. Lithium, the drug of choice for the treatment of bipolar mood disorder was discovered to possess anti-manic therapeutic potential by John Cade in 1949. The first anti-psychotic medication, chlorpromazine was discovered by Delay & Deniker in 1952. Similarly the first tricyclic antidepressant, imipramine, as well as the first benzodiazepine anti-anxiety drug, chlordiazepoxide, were discovered in 1957 (Table 2).

TABLE 2

Modalities of Psychopharmacological Treatments Discovered in the 1950s

| Treatment Modality | Prototypical | Discoverer of Medication | Year |
|---|---|---|---|
| Mood stabilizer | Lithium | J. F. J. Cade | 1949 |
| Anti-psychotic | Chlorpromazine | J. Delay & P. Deniker | 1952 |
| Anti-depressant: | | | |
| Tricyclic | Imipramine | R. Kuhn | 1958 |
| MAO-inhibitor | Iproniazid | N. S. Kline | 1958 |
| Anti-anxiety | Chlordiazepoxide | Randell | 1957 |

From that bifurcating time point in the history of psychopharmacology only few new treatment modalities i.e., anti-obsessive-compulsive medications, have appeared, and only few improvements in clinical efficacy of the existing treatment modalities have came upon. Based on pathophysiological hypotheses, new drugs (e.g. serotonin-selective re-uptake inhibitors as new antidepressants, dopamine-serotonin antagonists as new anti-psychotics) have been developed. The most notable improvements exist in the development of medications with fewer side effects.

The existence of biological-pharmacological treatments in mental disorders has appropriated psychiatry as a medical discipline. The medical model has become the dominant mode of psychiatry world-wide. In this model psychiatrists are seen as physicians who specialize in the treatment of mental disorders. Diagnosis is used to predict the future course of a disorder and its likely response to treatment, and it is the foundation for all subsequent therapeutic decisions. In contrast, the adaptation model used by psychoanalytic psychiatry for example sees psychiatrists as specialists in behavior and adaptation whose expertise can benefit people whether or not they have a diagnosable mental disorder.

There is a significant gap between advances in medication for mental disorders and the present static situation in diagnosis and monitoring treatments of these disorders. As with all areas of medicine, treatment decisions are guided by diagnosis. Unlike most disciplines of physical medicine, psychiatry has no external validating criteria. The present categorical classification of mental disorders and, accordingly, differential diagnosis in Psychiatry, divides mental disorders into types based on clusters of clinical signs, symptoms and their time course. The current Diagnostic and Statistical Manual of Mental Disorders (DSM-IV) of the American Psychiatric Association and International Statistical Classification of Diseases and Related Health Problems classification of mental disorders (ICD-10, Chapter V), developed by the World Health Organization, both use an empirical, non-theoretical orientation and operational criteria, which are predominantly phenomenological. These classification systems use explicit diagnostic criteria, and a descriptive approach that attempts to be neutral with respect to theories of etiology (e.g. biological psychiatry, psychoanalysis). DSM and ICD categorical classification divides mental disorders into types based on clusters of clinical signs, symptoms and their time course. Table 3 exemplifies DSM-IV criteria for major depressive episode.

TABLE 3

DSM-IV Criteria for Major Depressive Episode

1. Five (or more) of the following symptoms have been present during the same 2-week period and present a change from previous functioning; at least one of the symptoms is either (1) depressed mood or (2) loss of interest or pleasure.
  (1) Depressed mood most of the day, nearly every day, as indicated by either subjective report (e.g., feels sad or empty) or observation made by others (e.g., appears tearful).

TABLE 3-continued

DSM-IV Criteria for Major Depressive Episode (2) Markedly diminished interest or pleasure in all, or almost all, activities most of the day, nearly every day.
(3) Significant weight loss when not dieting or weight gain (e.g., a change of more than 5% of body weight in a month), or decrease or increase in appetite nearly every day.
(4) Insomnia or hypersomnia nearly every day.
(5) Psychomotor agitation or retardation nearly every day.
(6) Fatigue or loss of energy nearly every day.
(7) Feelings of worthlessness or excessive or inappropriate guilt nearly every day.
(8) Diminished ability to think or concentrate, or indecisiveness, nearly every day.
(9) Recurrent thoughts of death, recurrent suicidal ideation without a specific plan, or a suicidal attempt or a specific plan for committing suicide.
1. The symptoms do not meet criteria for a Mixed Episode (Manic and Major Depressive Episode).
2. The symptoms cause clinically significant distress or impairment in social, occupational, or other important areas of functioning.
3. The symptoms are not due to the direct physiological effects of a substance or a general medical condition.
4. The symptoms are not better accounted for by Bereavement.

In contrast to the exciting advances made in the psychopharmacology of mental disorders and in spite of a considerable research effort directed at attempting to decipher the biological underpinnings of psychiatric disorders, no biochemical cross-diagnostic tests capable of supporting psychiatric differential diagnosis and treatment monitoring are available. Although the structured algorithms described in the DSM and ICD diagnostic systems have been extensively tested and revised to improve their reliability and validity, these diagnostic criteria rely upon subjective reports by the patients and subjective elements in their evaluation by psychiatric specialists. There are presently no reliable, sensitive and specific objective biological diagnostic markers that can serve as 'gold standards'.

The importance of a biochemical assay for major depression lays in the ability, both by the general practitioner, who treats about half of these patients, and by mental health professionals, to decide on the application and follow up of biological antidepressant treatments. While it is recognized that significant morbidity and mortality is associated with depression, failure to appropriately diagnose individuals remains the primary obstacle to the effective management of this disorder. The results of the NIMH Epidemiologic Catchment Area program, which assessed mental disorder prevalence, incidence and service use in about 20,000 community and institutional residents have shown that there is limited treatment of individuals in the community diagnosed with psychiatric disorders. Concerning mood disorders, for example, only 11% of individuals with major depression had received an antidepressant medication. When individuals with major mental disorders seek treatment, they are usually underdiagnosed, or if correct diagnosis is made, they receive inadequate psychopharmacological intervention. More than 50% of the population who seek treatment for mental disorders usually turn to general practitioners and other physicians other than psychiatrists. Less than 50% of those who turn to general practitioners for depressive illness are diagnosed properly. Less than 50% of those who are properly diagnosed by the general practitioner receive the proper medicative treatment. Less than 50% of those who do receive proper pharmacological treatment by the general practitioner, receive the proper dosage.

The Medical Outcomes Study, a four-year longitudinal study of more than 20,000 patients with chronic conditions in different practice settings in the United States, found that depressed patients who consulted a family physician in a fee-for-service setting had roughly a 55% chance of having their condition diagnosed correctly. The detection rate for patients consulting primary care physicians in managed care organizations was even lower: approximately 40%.

The serendipitous discovery of antidepressant medications more than 50 years ago provided the first evidence of an inherent biochemical abnormality underlying the disorder. The 'pharmacocentric' approach to the construction of biological hypotheses for pathogenesis of mental disorders is trying to induce from knowledge and hypotheses concerning the biochemical mechanism of action of neuropsychiatric medications to pathogenic and pathophysiologic hypotheses. Research into the mechanism of action of the first tricyclic antidepressant imipramine and the first monoamine oxidase inhibitor-type of antidepressant iproniazide, has shown that increasing synaptic concentrations of monoamines (re-uptake inhibition of serotonin and/or norepinephrine to presynaptic vesicles;

monoamine oxidase inhibition) can improve the symptoms of depression. Thus a role for monoaminergic mechanisms in the pathogenesis of mood disorders has been formulated in the catecholamine, the serotonin, and the monoaminergic-cholinergic balance hypotheses of, mood disorders. The monoaminergic hypothesis did not provide an adequate explanation to the lag period of 10-20 days in the therapeutic actions of antidepressants. Thus, in the mid-1970s, theories on the mode of action of antidepressants shifted the emphasis from acute pre-synaptic events to delayed post-synaptic adaptations at the level of receptors.

Antidepressants are well known for their potential to modulate the density of functional neurotransmitter receptors such as beta adrenergic receptors in the brain, as well as in cultured cells. Beta-adrenergic down-regulation is accompanied by decreased receptor-stimulated cAMP formation. The mechanisms for this reduction in receptor numbers are not completely understood. Importantly, the onset of down-regulation and clinical effectiveness requires 10-20 days of antidepressant treatment. It has been proposed that the reduction in the number of functional beta-adrenergic and other receptors could be a regulatory response to the enhanced presence of the neurotransmitter in the synaptic cleft. The neurotransmitter's elevated concentration is induced by acute inhibition of its reuptake or of monoamine oxidase activity by antidepressants. Some clinically effective antidepressants, however, neither influence norepinephrine or serotonin reuptake nor inhibit monoamine oxidase activity but still cause receptor down-regulation. Furthermore, this model fails to explain the observed time lag between the rapid drug-induced increase in intra-synaptic neurotransmitter concentrations and the delayed receptor down-regulation.

Decreased monoamine receptors densities following antidepressant treatment can also be seen in cell culture systems lacking a presynaptic input. Thus, monoamine receptor down-regulation may directly result from post synaptic actions of the antidepressants. Very recent studies suggest that antidepressants might induce switch of beta-adrenergic receptor trafficking as a mechanism for their action.

It has recently been found that there are signal transduction components involved in receptor desensitization.

Almost all G protein coupled receptors are tightly regulated by a common desensitising mechanism. The process of agonist-specific, homologous desensitization of receptors is characterized by an increase in the refractoriness of a receptor to signal in response to repeated or sustained exposure to its agonist, limiting both the magnitude and the temporal extend of the receptor signal, thus protecting cells from over-stimulation. The waning of G-protein-coupled-receptor (GPCR) signaling in the continued presence of agonist is accomplished by a coordinated series of events that are typically considered as three distinct processes:

(i) receptor desensitization—mediated by uncoupling the activated receptor from its specific G protein and achieved within a few minutes following agonist exposure;

(ii) receptor sequestration or endocytosis—mediated by receptor internalization from the plasma membrane to early endosomes, a process that occurs more slowly than desensitization, happening over a period of several minutes to hours after agonist exposure;

(iii) down-regulation—receptor degradation, a process that leads to a reduction in the total number of receptors.

The mechanism underlying the phenomenon of desensitization involves the activities of two families of proteins: G protein-coupled receptor kinases (GRKs), and arresting. GRKs comprise a highly regulated cytosolic, multigene family of serine-threonine kinases, capable of specifically phosphorylating the agonist-occupied form of GPCRs. Receptor phosphorylation by GRKs has been ultimately identified as the initial and critical step in the uncoupling of receptor from G protein leading to the attenuation or desensitization of GPCR signaling. GRKs are translocated to the plasma membrane for their appropriate interaction with receptor domains. It is known that free G protein βγ subunits bind to the C-terminal domain of GRK and facilitate the translocation process. Today seven GRKs have been identified, two of them specific to the visual system (GRK1 & 7), one selectively present in sperm cells (GRK4), and four ubiquitously distributed.

Activated heptahelical receptors are phosphorylated by a family of G protein-coupled receptor kinases (GRKs). Following phosphorylation, the receptors bind to another family of proteins called arresting. Arrestin is the name given to a class of soluble proteins that are found to stop or 'arrest' intracellular signaling triggered by G protein coupled transmembrane receptors. The regions of the receptors that arrestins bind to, are also primary determinants for G protein interaction. Arrestin binding to receptors thus results in desensitization of G protein-mediated signaling by preventing interaction of receptors with G proteins. To date, four members of the arrestin gene family have been cloned. Two arrestins, visual arrestin and cone arrestin, are expressed almost exclusively in the retina, where they regulate photoreceptor function, while β-arrestin1 and β-arrestin2, are ubiquitously expressed proteins. Although most of the research regarding the desensitization process has been carried out using the beta-2-adrenergic receptor as a model, it is now clear that this process regulates the function of many GPCRs, including α- and β-adrenergic, muscarinic cholinergic, serotonergic, dopamine, angiotensin, endothelin, etc.

An emerging view, however is that the binding of arrestins to heptahelical receptors also initiates a new set of signaling pathways in addition to blocking those mediated by G protein activation. The association of arrestins with heptahelical receptors does not simply uncouple receptors from G protein pathways, but rather induces a switch in receptor signaling from classical second messenger-generating G protein-mediated pathways to other pathways such as those involving tyrosine kinases of the Src family, and leading to activation of MAP kinase. Moreover, arrestins have also been found to interact with a number of cellular proteins involved in endocytosis such as clathrin. Thus arrestins may well represent multifunctional adaptor proteins that mediate a number of aspects of heptahelical receptor signaling. GRKs may also be signaling intermediates for heptahelical receptors rather than just proteins involved in receptor desensitization. Recently, it was found that GRK2 can associate with actin and tubulin and can phosphorylate tubulin. Thus the recruitment of GRKs to activated heptahelical receptors may lead to cytoskeletal regulation or to modulation of other intracellular processes.

A differential pattern of receptor-coupled G protein measures was detected in mononuclear leukocytes of patients with the major mental disorders of mania, depression, schizophrenia, and panic disorder. G protein measures were suggested as a possible differential diagnostic test for these disorders [Table 4].

TABLE 4

Differential G Protein Measures in Leukocytes of Patients with Mental Disorders

| Disorder | G protein function | G protein level | G protein altered measure |
|---|---|---|---|
| | Agonist - enhanced Guanine nucleotide binding | Immunoreactivity | Normalization by specific treatment |
| Mania | Increased β-Gs | Increased Gαs | Lithium |
| | Increased M-Gi | Increased Gαl | Lithium |
| Depression | Decreased β-Gs | Decreased Gαs | Antidepressants, ECT |
| | Decreased M-Gi | Decreased Gαi | Antidepressants, ECT |
| Winter Depression | | Decreased Gαs | Light therapy |
| In SAD | | Decreased Gαl | Light therapy |
| Schizophrenia | Normal-like β-Gs | Normal-like Gαs | Antipsychotics |
| | Normal-like M-Gi | Normal-like Gαl | Antipsychotics |
| | Increased D-Gs | | Antipsychotics |
| Panic | Increased β-Gs | Normal-like Gαs | |
| | Decreased M-Gi | Normal-like Gαi | |

β-Gs: β-adrenergic receptor coupled Gs protein function;
M-Gi: Muscarinic receptor coupled Gi protein function;
D-Gs: Dopamine receptor coupled Gs protein function.

[for review see Avissar & Schreiber, 2002; Schreiber & Avissar, 2003]. G protein measures were also applied as an objective measure of depression in patients with irritable bowel syndrome.

The ability to detect state-dependent, disorder-specific alterations in G protein measures in patients with major depressive disorder, mania, panic disorder and schizophrenia, supported the use of these measures to biochemically monitor normalization of altered G protein measures during specific treatments [Table 4]. Indeed the elevated function of Gs and Gi proteins detected in patients during a manic episode was normalized by lithium treatment. Reduced Gs and Gi proteins level and function in patients during a depressive episode were corrected by antidepressants and ECT. The dynamics of normalization by electroconvulsive treatment of the biochemical measures of $G_s$ and $G_i$ function and of $G\alpha_s$ and $G\alpha_i$ levels was found not to follow and thus reflect the clinical improvement of the depressed patients, but rather to precede clinical improvement. The biochemical findings preceded clinical improvement by at least 1½ week. In SAD patients the extent of normalization of G protein measures by light therapy segregated well between responders and non-responders to light therapy.

Use of the state dependency of G protein measures in mood disordered patients was suggested as a mean to monitor and predict response to antidepressant treatments. It is very difficult to monitor the extent of clinical response especially in the early period of the first and second week after initiation of antidepressant treatment. Clinical response to antidepressant treatments is due both to the specific biochemical antidepressant effects of the medication, as well as to placebo effects. Since the placebo effect is usually more pronounced during the early period of treatment initiation, it is very difficult to assess in these early days the specific antidepressant effects of antidepressant treatments. G protein measures in peripheral blood elements of patients with mood disorders, as a state dependent characteristic, may afford biochemical monitoring and prediction of clinical response.

Dopamine-induced Gs hyperfunction characteristic of untreated patients with schizophrenia was corrected by treatment with either the classical anti-psychotic haloperidol and the newer anti-psychotic clozapine [Table 4]. Haloperidol caused a significant decrease in Gs level and function to below normal levels, characteristic of patients with Parkinson's disease. The extend of reduction in Gs measures was found to be correlated with the intensity of the Parkinsonian side effects, enabling the biochemical monitoring not only of anti-psychotic effects, but also of the extend of parkinsonian side effects.

Thus, according to the present invention there is now provided a diagnostic composition for detecting an affective disorder comprising an antibody selected from the group consisting of an antibody to a beta-arrestin, an antibody to a G-protein coupled receptor kinase and combinations. thereof as the active detecting agent therein.

In preferred embodiments of the present invention there is provided a diagnostic composition for detecting depression comprising an antibody selected from the group consisting of an antibody to a beta-arrestin, an antibody to a G-protein coupled receptor kinase and combinations thereof as the active detecting agent therein.

The invention also provides a composition for monitoring the effectiveness of an antidepressant, said composition comprising an antibody selected from the group consisting of an antibody to a beta-arrestin, an antibody to a G-protein coupled receptor kinase and combinations thereof as the active monitoring agent therein.

In another aspect of the present invention there is provided a method for diagnosing an affective disorder, or gauging the effect of a treatment upon a patient suffering from an affective disorder comprising determining the level of a beta-arrestin present in a patient and diagnosing the affective disorder or gauging the effect of the treatment upon the patient based on said determination.

SUMMARY

Preferably, said method comprises determining the level of a blood component selected from the group consisting of a beta-arrestin, a G-protein coupled receptor kinase and combinations thereof and diagnosing the affective disorder or gauging the effect of a treatment upon the patient based on said determination.

In preferred embodiments of the present invention there is provided a method for gauging the effect of a treatment upon a patient with an affective disorder comprising determining the level of a blood component selected from the group consisting of a beta-arrestin, a G-protein coupled receptor kinase and combinations thereof, before and during treatment and comparing said level to that expected of a healthy person.

In especially preferred embodiments of the method of the present invention said affective disorder is depression and an increase in the level of a G-protein coupled receptor kinase towards normal values is indicative of a positive effect of a treatment.

In other especially preferred embodiments of the method of the present invention said affective disorder is depression and an increase in the level of beta-arrestin towards normal values is indicative of a positive effect of a treatment.

In yet preferred embodiments of the method of the present invention said affective disorder is a bi-polar personality disorder and an increase in the level of beta-arrestin towards normal values is indicative of a positive effect of a treatment.

In yet other preferred embodiments of the method of the present invention said affective disorder is a bi-polar personality disorder and an increase in the level of a G-protein coupled receptor kinase towards normal values is indicative of a positive effect of a treatment.

In another aspect of the present invention there is provided a kit for diagnosing an affective disorder by monitoring the level and function of a blood component selected from the group consisting of a beta-arrestin, a G-protein coupled receptor kinase and combinations thereof, said kit comprising an antibody selected from the group consisting of an antibody to a beta-arrestin, an antibody to a G-protein coupled receptor kinase and combinations thereof as the active agent therein and the manufacturer's instructions for using the kit.

While the invention will now be described in connection with certain preferred embodiments in the following examples and with reference to the accompanying Figures so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

IN THE DRAWINGS

DETAILED DESCRIPTION

EXAMPLE 1

Figure 1:
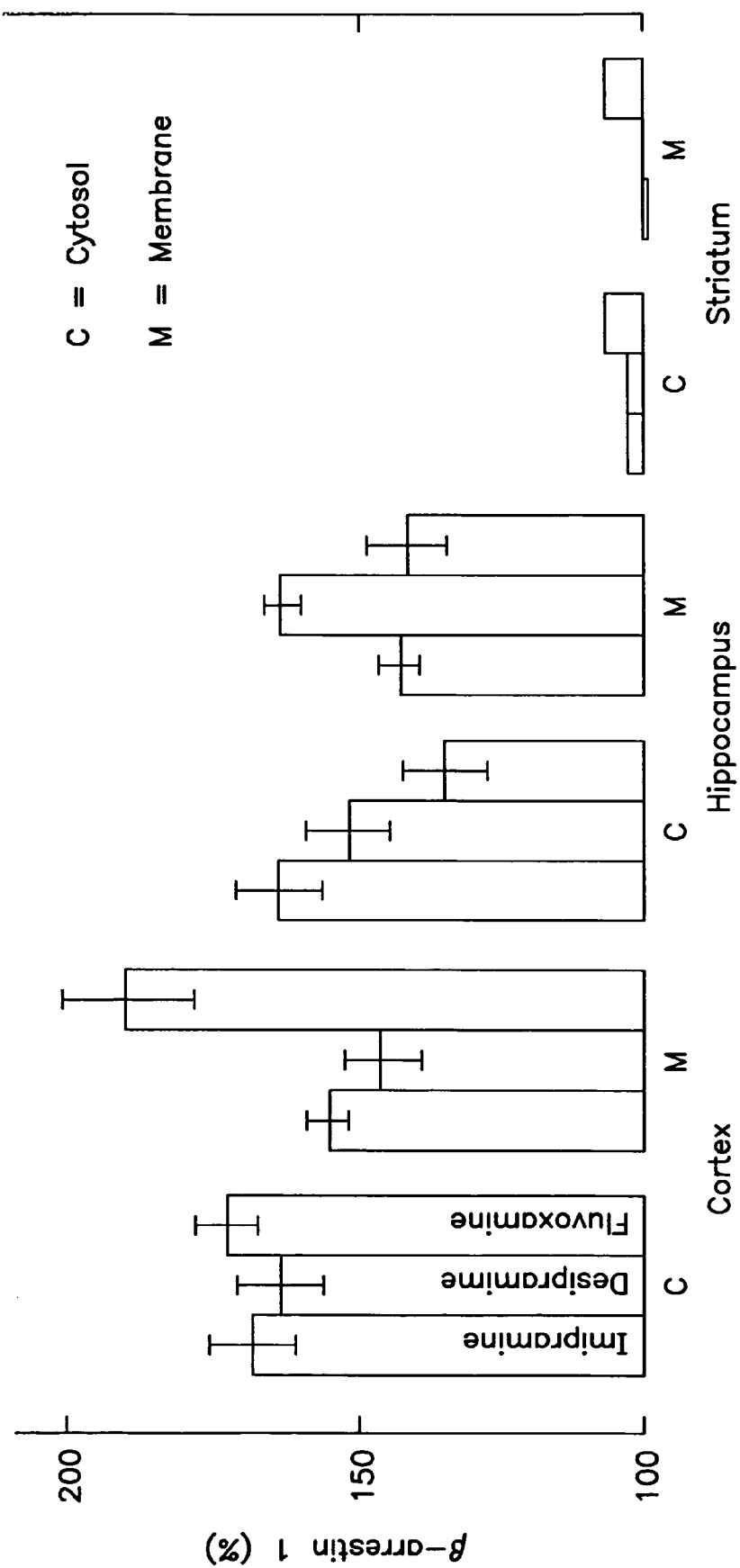
FIG. 1 is a graphical representation of both cytosolic and membrane levels of beta-arrestin 1.

All patients were diagnosed according to DSM-IV criteria by at least two senior psychiatrists. Inclusion criteria were normal results of physical examination, electrocardiogram, and laboratory tests for renal, hepatic, hematologic, and thyroid function. After complete description of the study to the subjects, written informed consent was obtained for a 20-60 ml blood donation. In all cases blood was drawn between 8:00-10:00 A.M. The Hamilton Depression Inventory was administered before blood donation. The study was approved by the Institutional Review Board.

The group of 36 untreated patients with major depression consisted of 27 (14 female and 13 male) patients (average age 41.9, SD=12.3, range 19-71) with Hamilton score≧21, who were found to meet the inclusion criterion of Ham-D≧21 and 9 untreated patients with Hamilton score 10-20, whose beta-arrestin measures were included only in the correlation between beta-arrestin levels and Ham-D. Patients were examined before the initiation of treatment. The healthy volunteer group consisted of 32 subjects (18 female and 15 male), average age 39.2 (SD=12.6, range 20-75) years, from the staff and staff's families of Ben Gurion University. A group of 14 untreated patients with major depression consisting of 9 female and 5 male patients (average age 36.6, SD=15.3, range 18-58)with Hamilton score≧18, were examined for both beta-arrestin1 protein and mRNA levels, before the initiation of treatment and at one, two and four weeks after initiation of treatment. Patients were blindly assigned in advance to receive either the SSRI: citalopram or the SNRI: venlafaxine. Half of the patients (7 patients) received citalopram 20-40 mg/d, while the other half of the patients (7 patients) received venlafaxine 150-225 mg/d. The healthy volunteer group consisted of 14 subjects (9 female and 5 male), average age 37.1 (SD=12.6, range 19-57) years, from the students and staff of Ben Gurion University.

EXAMPLE 2

Rat Chronic Treatment with Antidepressant Drugs

Male rats (Sprague-Dawley, 250 g) were chronically treated for 21 days by intragastrical treatment with either imipramine, desipramine or fluvoxamine, 10 mg/kg, twice daily. Control rats were intragastrically treated with either distilled water or 10% ethanol, used as vehicle for imipramine/desipramine or fluvoxamine, respectively. No significant differences were found between the two groups of control animals. On the $22^{nd}$ day, rats were decapitated, blood collected and brain regions immediately dissected. Tissue homogenization was carried out in a glass-teflon homogenizer with ice-cold buffer containing 20 mM Tris.Cl pH 7.4, 2 mM EDTA, 1 mM DTT and antiprotease cocktail (Sigma). After initial centrifugation at 800 g for 5 min, the supernatant was collected and further centrifuged at 48,000 g for 30 min using a Beckman Ti80 rotor. The resulting supernatant and pellet were separated: the supernatant fraction was collected and centrifuged at 120,000 g for 45 min and the supernatant obtained was used for all measurements; the pellet was resuspended in the homogenization buffer and the pellet fraction obtained was used for all measurements.

2a Determination of Antidepressant Levels:

Serum was prepared from blood collected at the time of decapitation and kept frozen for measurement of antidepressant levels. Imipramine and desipramine levels were measured by fluorescence polarization immunoassay in a TDx-FLx system (Abbott).

2b MNL Isolation

Mononuclear leukocytes were isolated from 50 ml heparinized fresh blood of adult donors, using Ficoll-Paque gradient. Cells were homogenized in 25 mM Tris-HCl, pH 7.4, 1 mM $Mg^{+2}$, 1 mM EGTA, 1 mM dithioreitol (DTT) and antiprotease cocktail (1:100) (Sigma). The cytolosic fraction (supernatant) was separated from the membrane fraction by centrifugation at 18,000 g for 20 min. Membranes were suspended in homogenization buffer and both fractions were frozen at −70° until assayed. Aliquots were taken for protein concentration determination using the Lowry assay.

2c Immunoblot Analysis

On the day of assay, cytosolic and/or membrane fraction were thawed. 10 μg total protein aliquots were taken for protein separation by SDS-(10%) polyacrylamide gel electrophoresis. The resulting proteins were transferred to nitrocellulose paper by use of electroblotting apparatus. Blots were blocked with 5% BSA for 1 hr in TBS containing 0.1% Tween-20 (TTBS) and incubated overnight with a monoclonal antibody to beta-arrestin1 (Transduction Labs, diluted 1:250). The immune bands were detected by subsequent incubation with anti-mouse IgG labeled with horseradishperoxidase using the Enhanced Chemiluminescence Western Blot Detection System (Amersham) followed by exposure to Kodak X-Omat film. The range of linearity of the assay as related to the protein concentration was found between 2.5-20 μg membrane-protein. Peak heights of immunoreactive bands presented as arbitrary absorbance units, were determined with a computer-assisted imaging system for semi-quantitative measurements. 10 μg rat cortical membranes run in each blot as a standard reference.

2-D Isolation of RNA and Reverse Transcriptase Polymerase Chain Reaction (RT-PCR):

Isolation and purification of total RNA from MNL was carried with EZ-RNA Kit (Beit Haemek, Israel). One-step RT-PCR (Abgene, England) was performed with oligonucleotide primers selected from the highly conserved nucleotide sequences of beta-actin (forward primer, 5'-CTACMTGAGCTGC GTGTGG-3'(SEQ ID NO:1), reverse primer, 5'-CGG TGAGGATCTTCATGA-3'(SEQ ID NO:2), amplified product 320 bp). To assess the specificity, beta-actin RNA served as an internal control for cDNA normalization. Normalized cDNAs were subjected to analysis of beta-arrestin1 (forward primer, 5'-CMGCCCTTGCACCTAGAAG-3'(SEQ ID:3), reverse primer 5'-GTTCGTGTCTTCGTGCTTGA -3' (SEQ ID NO:4), 316 bp). Primers were synthesized by Sigma Genosys, Israel. 1 μg of total RNA was used for RT-PCR in 25 μl reaction volume. After a denaturation step for 5 min at 94° C., thermal cycling was performed at 94° C. for 20 s, 50° C. for 30 s, 72° C. for 1 min, with a total number of 30 cycles for both beta-actin and beta-arrestin 1 gene products. After staining with ethidium bromide, amplified DNA fragments were separated by gel electrophoresis in 1% agarose. The relative density of the bands imprinted on the autoradiographic films was measured using a computerized image analysis system. PCR products were sequenced in both directions.

Results

Beta-arrestin—Major Depressive Disorder and its Treatment

Rats were treated for three weeks with three types of antidepressants: the non-selective monoamine re-uptake inhibitor imipramine; the norepinephrine specific re-uptake inhibitor desipramine; and the serotonin specific re-uptake inhibitor fluvoxamine. Beta-arrestin1 levels were measured in three rat brain areas: cortex, hippocampus and striatum. FIG. 1 shows that both cytosolic and membrane beta-arrestin 1 were significantly elevated by all three antidepressants in the cortex and in the hippocampus, while in the striatum no alterations in beta-arrestin 1 levels could be detected.

Cytosolic and membrane beta-arrestin 1 in rat cortex were significantly elevated under imipramine (Cytosolic beta-arrestin-1: 165.6%, SD14.3, t=5.5, v=32, p<0.001 ; and membrane beta-arrestin 1: 156.8%, SD26.3, t=5.53, v=27, p<0.001, respectively, Bonferroni t test for 3 treatment groups in comparison with a single control group), desipramine (163.4%, SD21.9, t=7.27, v=32, p<0.001 ; and 146.2%, SD18.3, t=5.35, v=27, p<0.001, respectively) and fluvoxamine (172.8%, SD15.6, t=10.3, v=32, p<0.001; and 190.1%, SD37, t=6.89, v=27, p<0.001, respectively) three weeks of treatment.

Cytosolic and membrane beta-arrestin-1 in rat hippocampus were significantly elevated under imipramine (179.2%, SD 27.8 , t=7.89, v=32, p<0.001; and 142.6%, SD10.4, t=6.27, v=26, p<0.001, respectively, Bonferroni t test for 3 treatment groups in comparison with a single control group), desipramine (151.6%, SD21.7, t=6.29, v=32, p<0.001 ; and 162.9%, SD27.7, t=5.3, v=26, p<0.001, respectively) and fluvoxamine (134.7% , SD22.3, t=4.14, v=32, p<0.001; and 140.8%, SD20.8, t=4.6, v=26, p<0.001, respectively) three weeks of treatment.

Figure 2A:
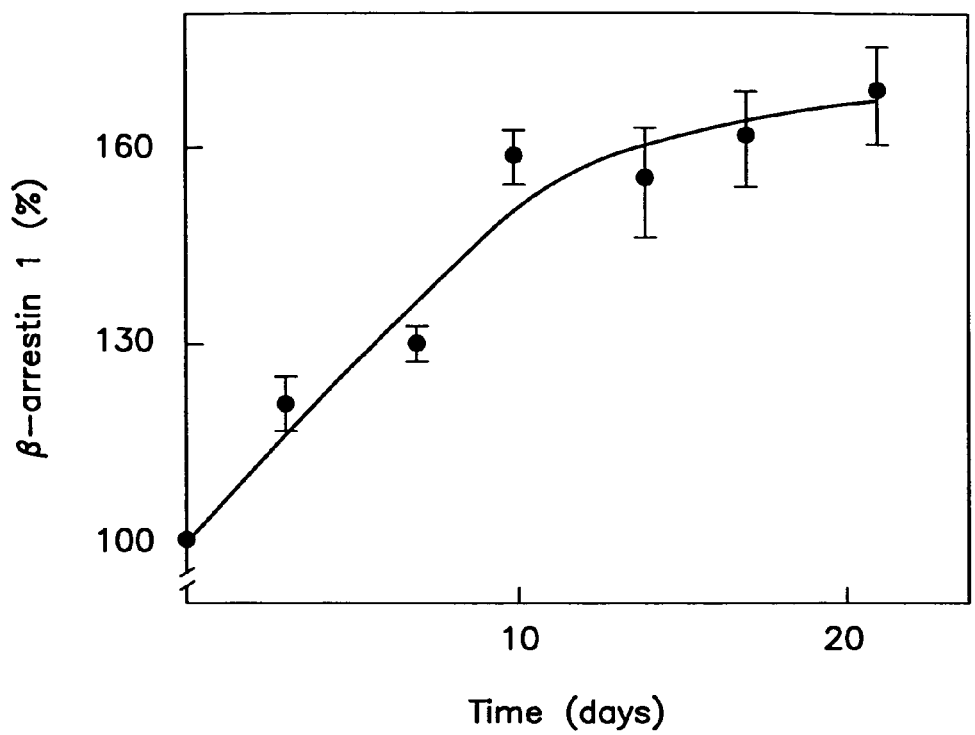
FIG. 2 is a graphical representation of increases in the level of both ctyosolic and membrante beta-arrestin-1.
Figure 2B:
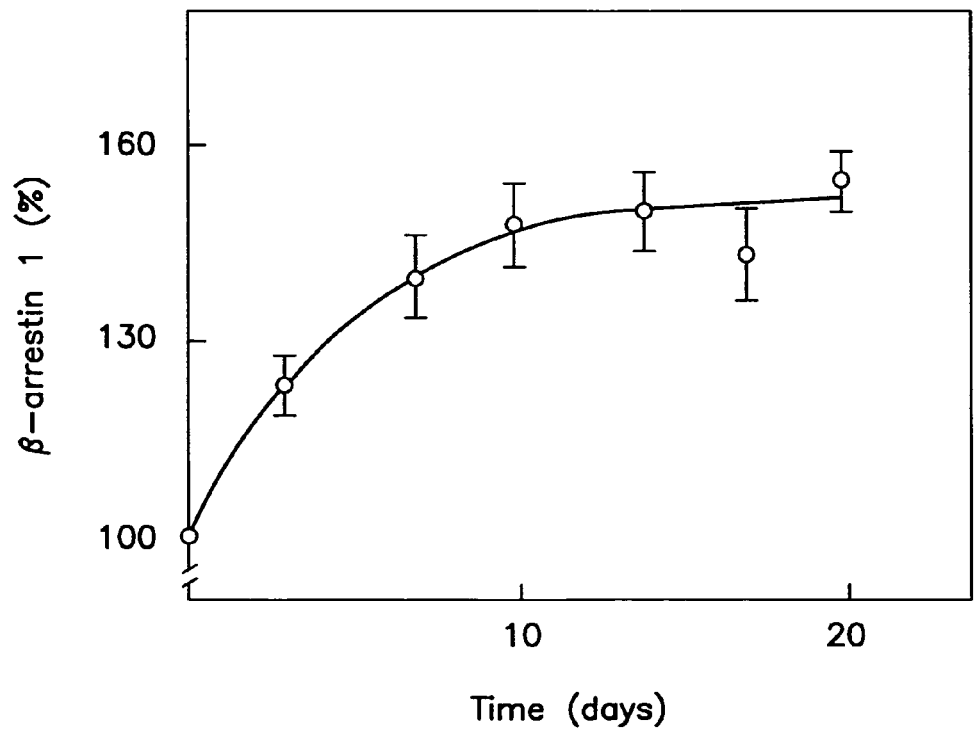
Figure 3A:
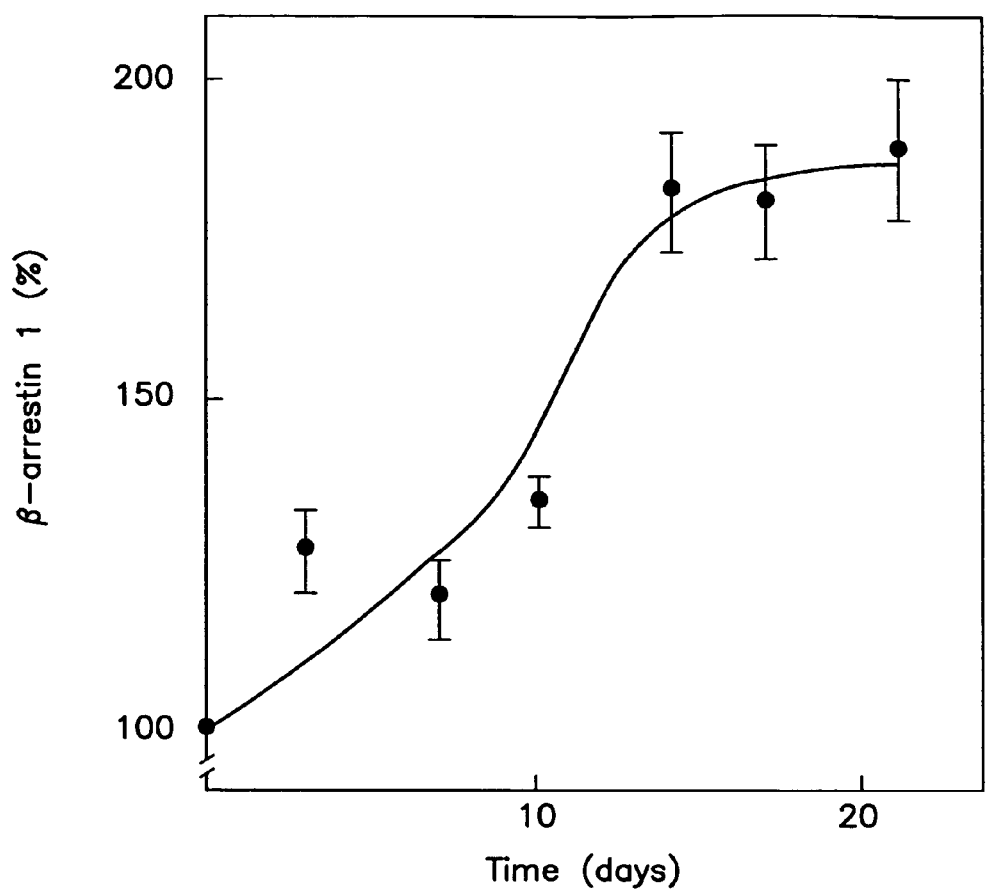
FIG. 3 is a graphical representation of increases in the level of both ctyosolic and membrante beta-arrestin-1.
Figure 3B:
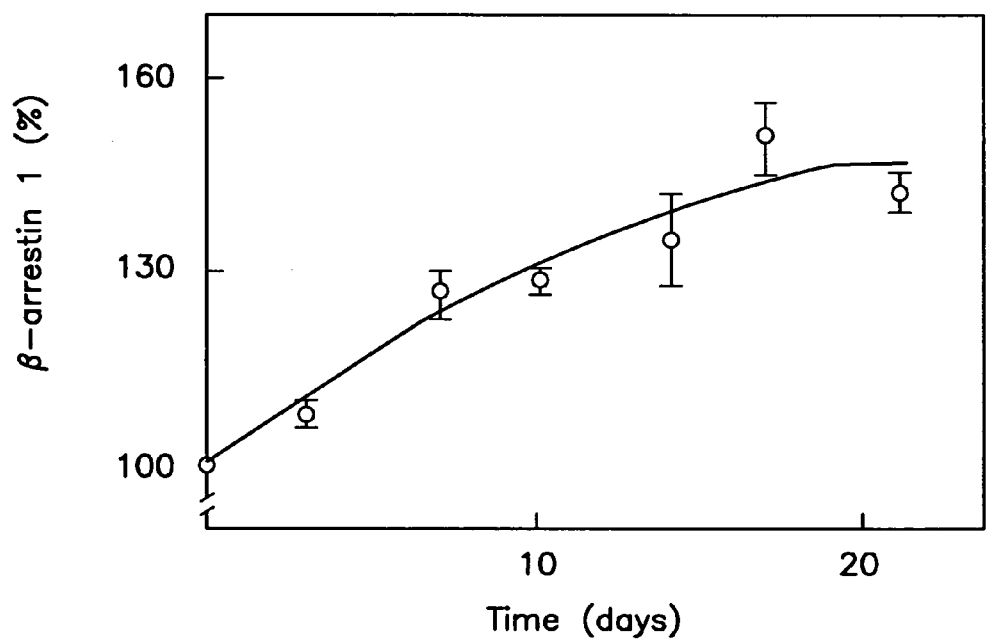

The dynamics of antidepressant-induced increases in the levels of both cytosolic and membrane beta-arrestin-1 indicate that the process became significant within 10 days and took 2-3 weeks to reach maximal increase (FIGS. 2 & 3).

Figure 4:
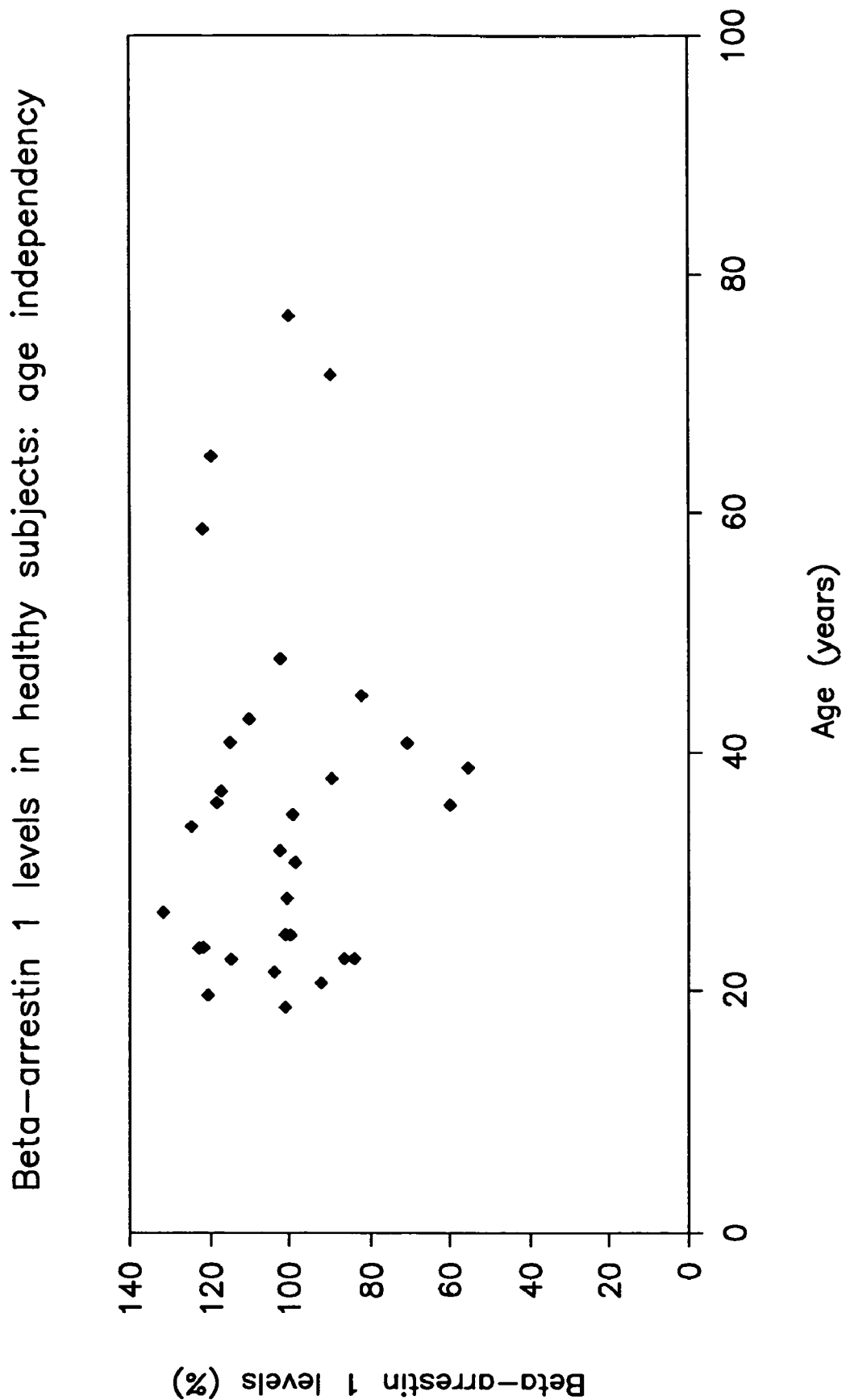
FIG. 4 is a graphical representation of beta-arrestin-1 levels in healthy subjects by age.
Figure 5:
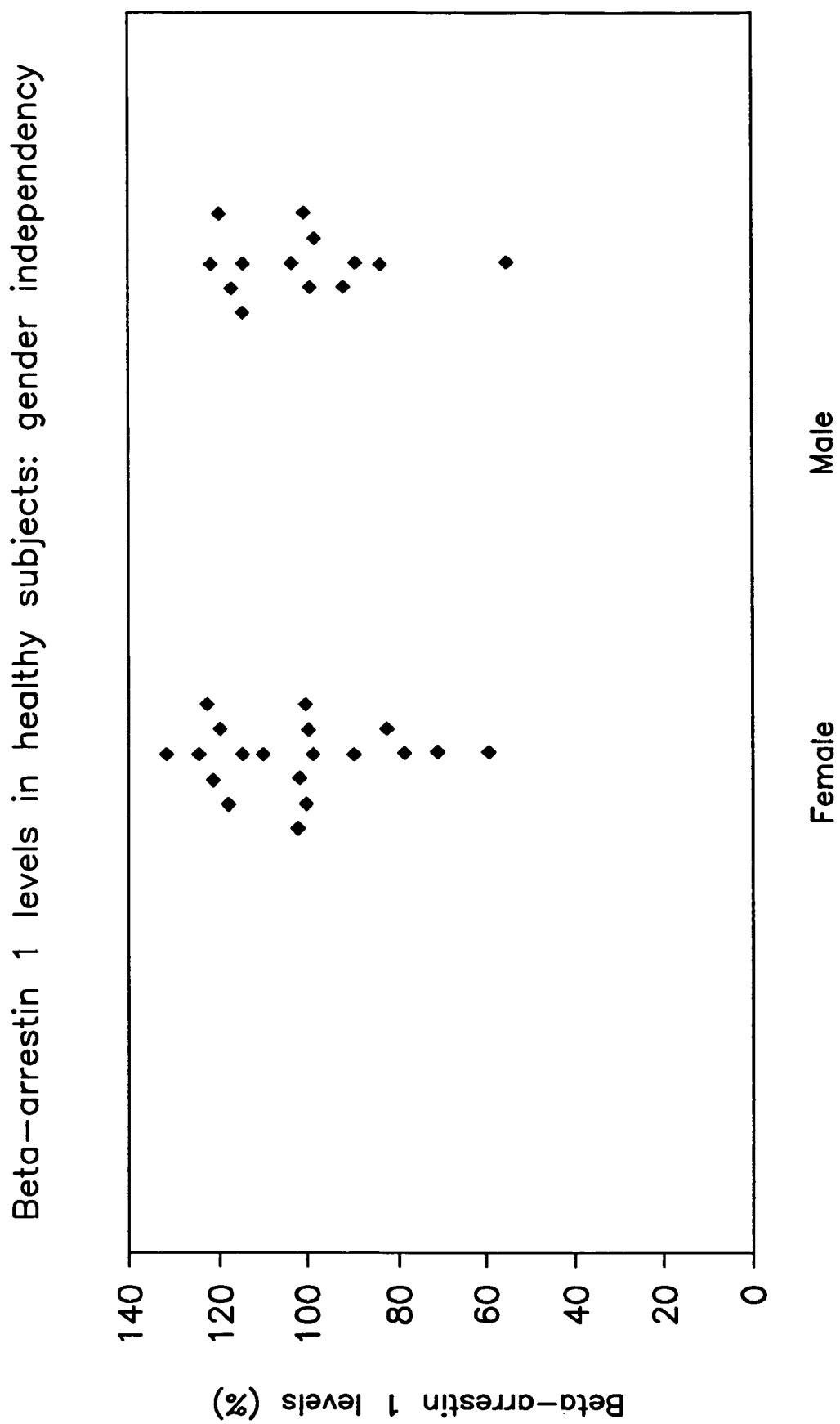
FIG. 5 is a graphical representation of beta-arrestin-1 levels in healthy subjects by gender.
Figure 6A:
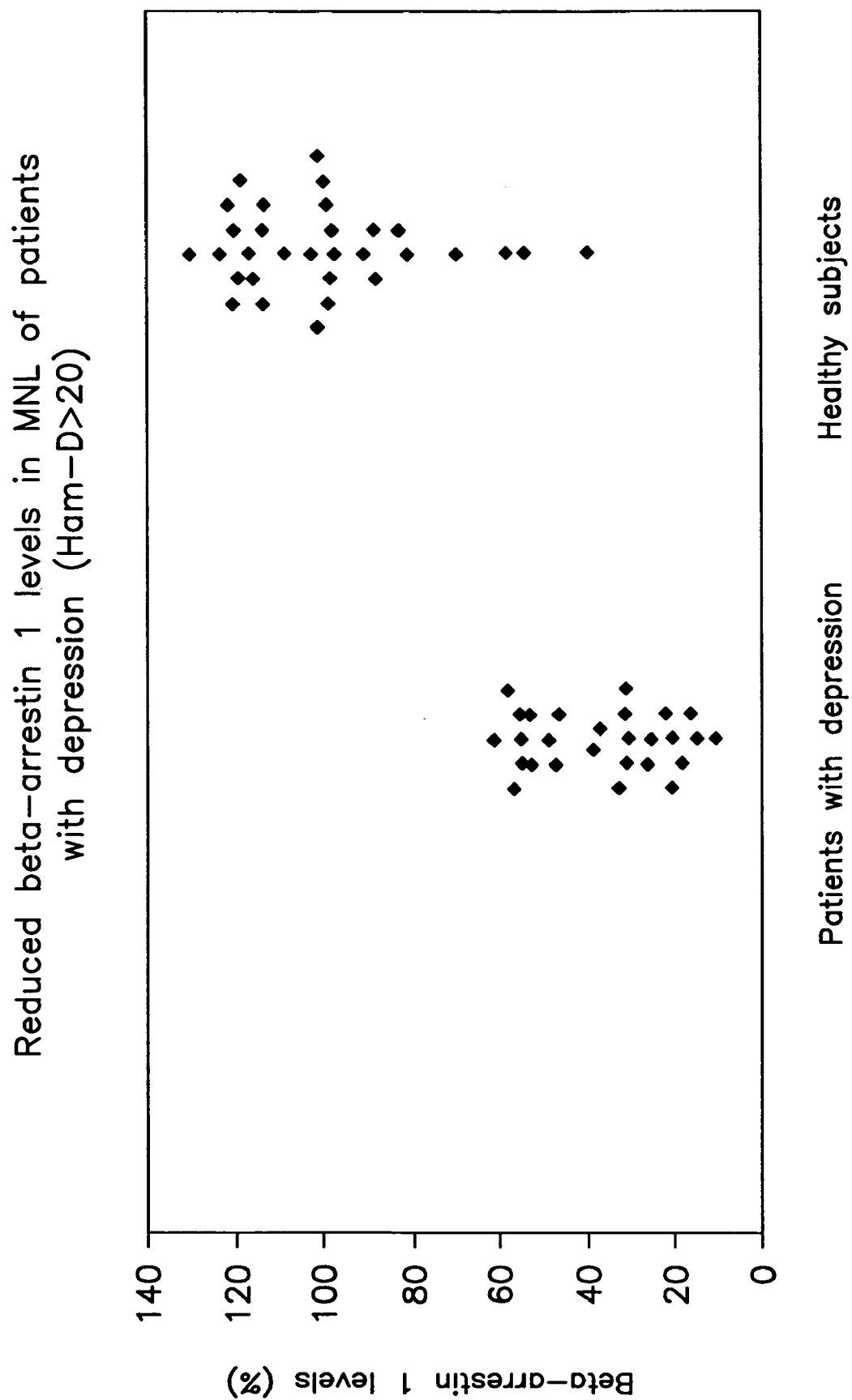
FIG. 6a is a graphical representation of reduced beta-arrestin-1 levels in MNL of patients with depression.
Figure 6B:
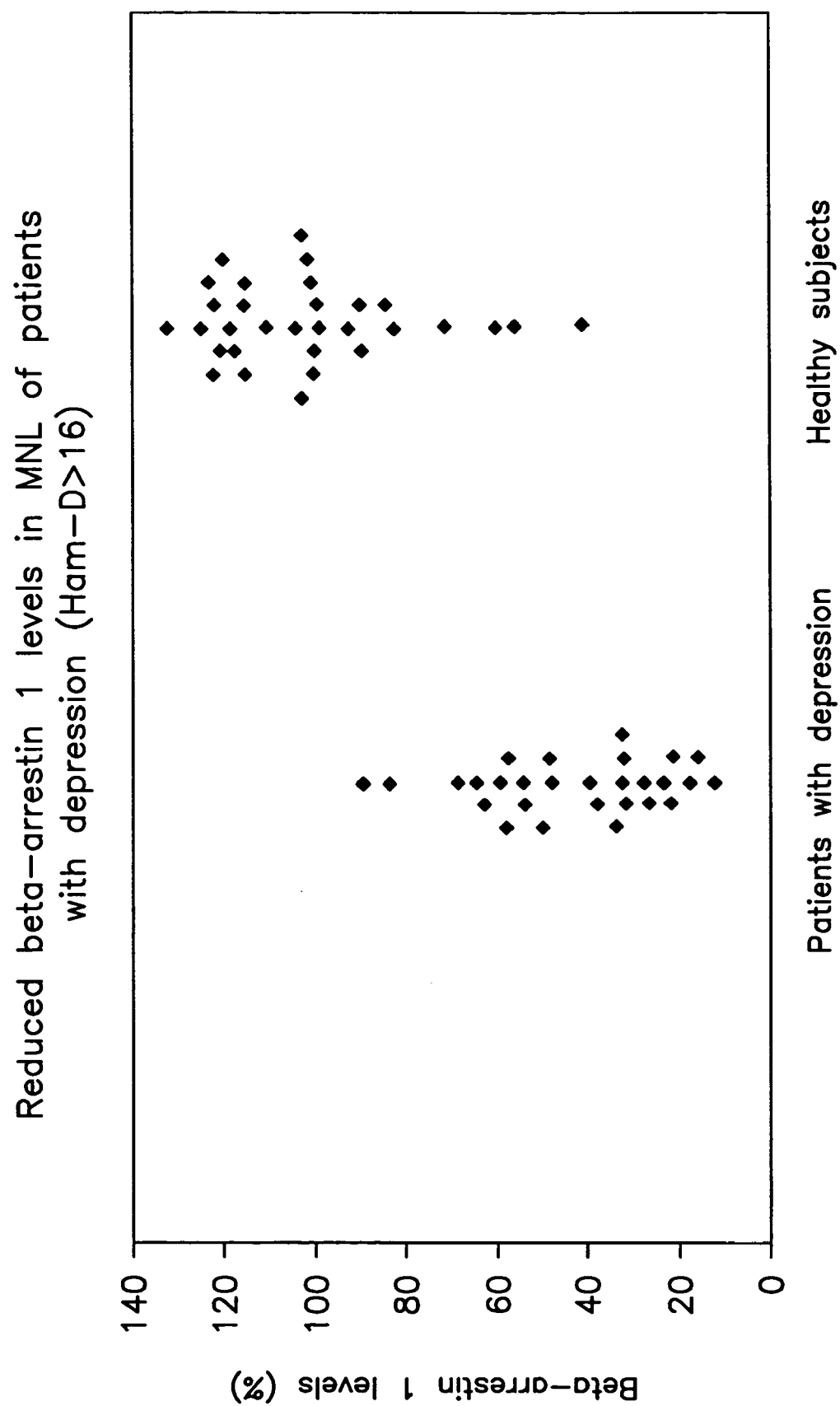
FIG. 6b is a graphical representation of reduced beta-arrestin-1 levels in MNL of patients with depression.
Figure 7:
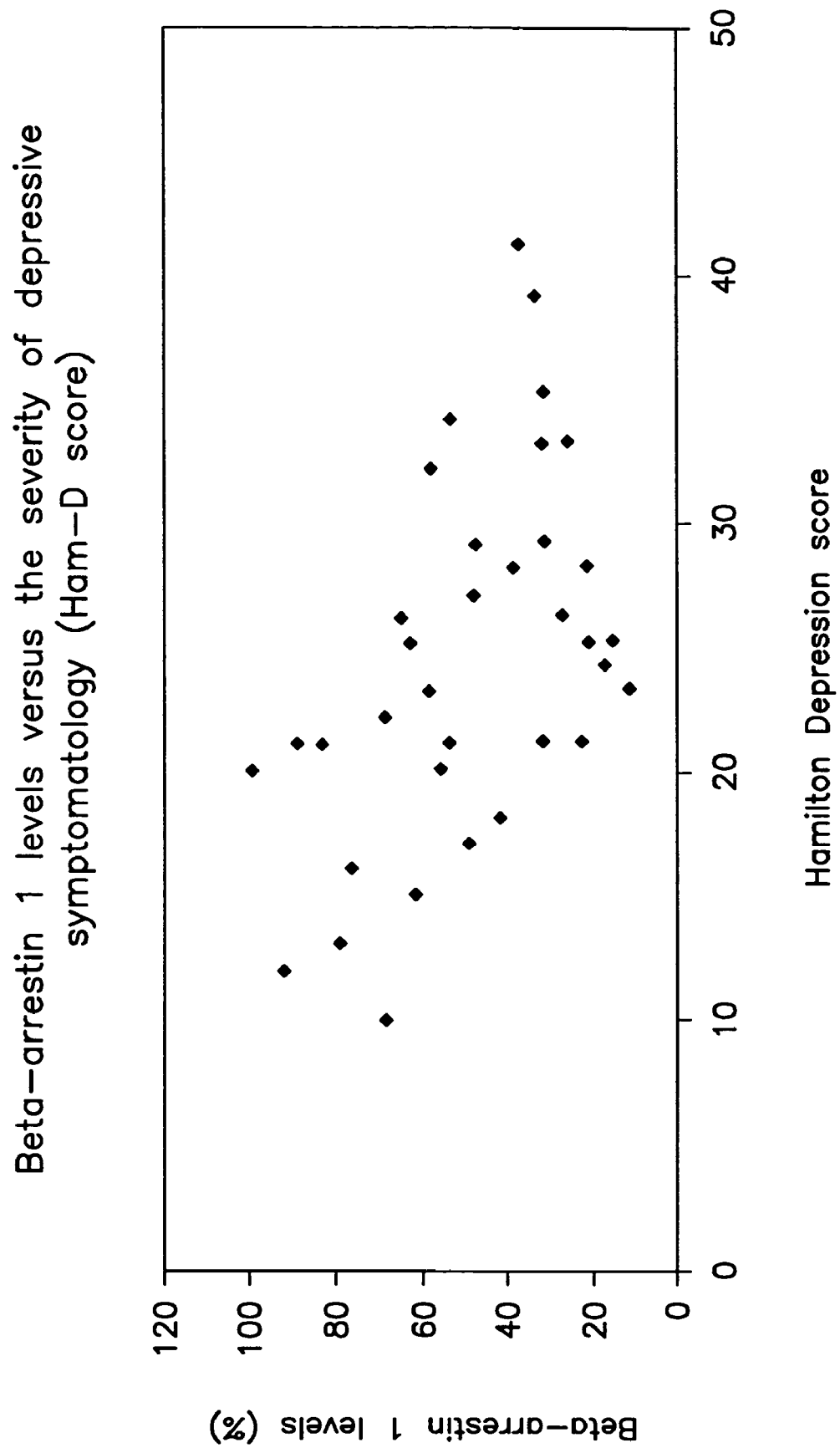
FIG. 7 is a graphical representation of beta-arrestin-1 levels versus the severity of depressive symptomatology.

The distinct elevations in the levels of beta-arrestin-1 induced by antidepressant medications in rat brain areas indicate that alterations in beta-arrestin-1 levels exist in humans suffering from a depressive episode. As it is known that beta-arrestin-1 is expressed in mononuclear leukocytes, these cells were chosen for our human experiments. Beta-arrestin-1 levels were evaluated in mononuclear leukocytes obtained from a group of patients diagnosed with major depressive episode, before the initiation of an antidepressant treatment, and compared with a group of healthy volunteers. Beta-arrestin-1 levels in the healthy volunteers group were independent of the age (Pearson's correlation coefficient=−0.06, N.S.) (FIG. 4) or gender (Average beta-arrestin-1 levels for female and male subjects, 101.0% and 99.0%, respectively. Us=135, ts=0.283, N.S., Mann-Whitney U-test) (FIG. 5) of the subjects examined. FIG. 6A shows that the levels of beta-arrestin-1 were significantly reduced in MNL of patients with major depressive disorder with ratings of Ham-D>20 (37.15%, SD=15.66%) in comparison with healthy volunteers (100.0%, SD=21.91%). The sensitivity and specificity of the findings for diagnosing major depressive episodes were found to be 92.5% and 93.9%, respectively. Including patients with depression with ratings on Ham-D of >16 (FIG. 6B) still resulted in high sensitivity and specificity values of 92.5% and 90.9%, respectively. The degree of reduction in MNL β-arrestin-1 levels was found to significantly correlate with the severity of the depressive episode evaluated by the Hamilton depression scale (Pearson's correlation coefficient=−0.661) (FIG. 7).

Figure 8A:
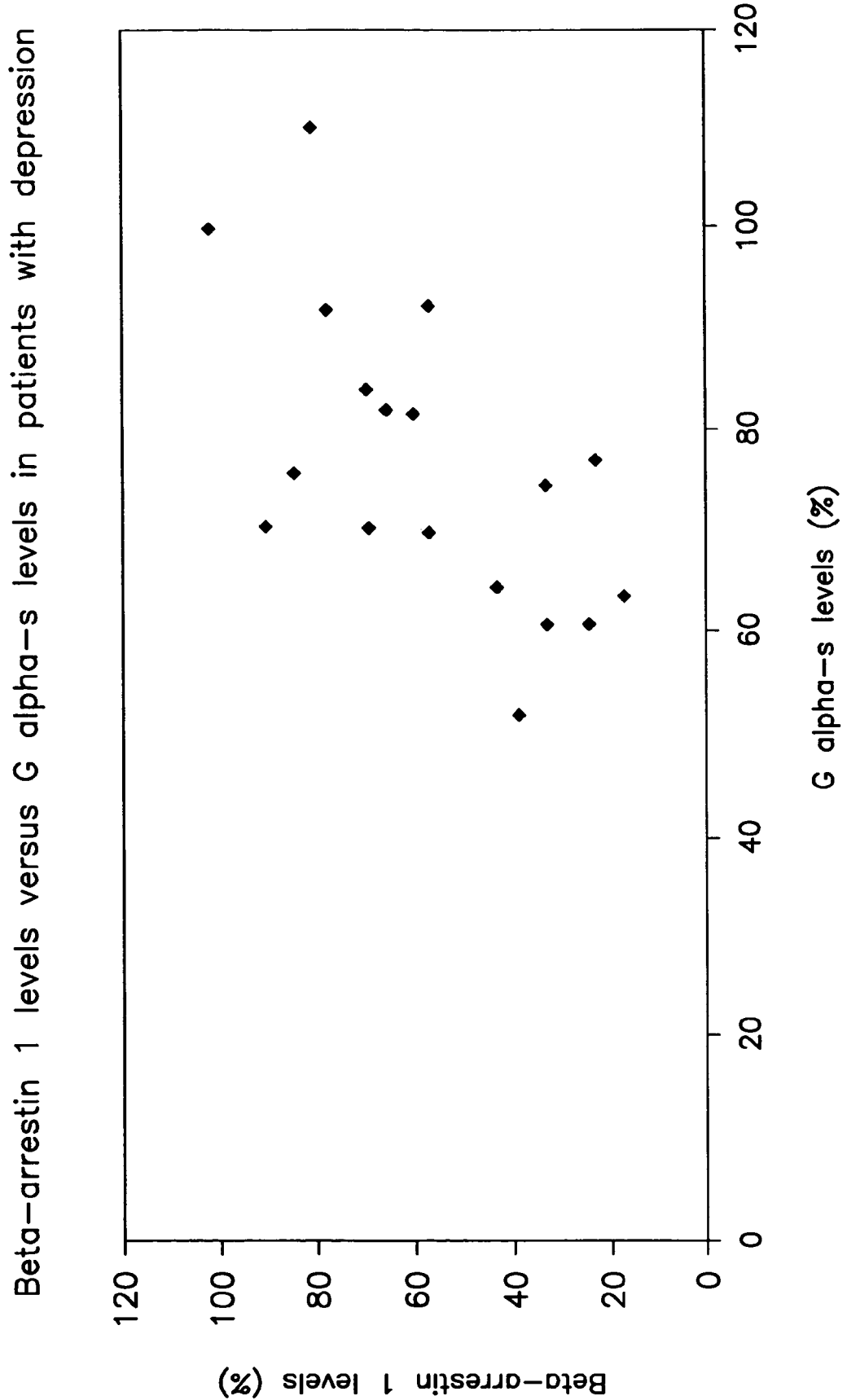
FIG. 8a is a graphical representation of beta-arrestin-1 levels versus G alpha-s levels in patients with depression.
Figure 8B:
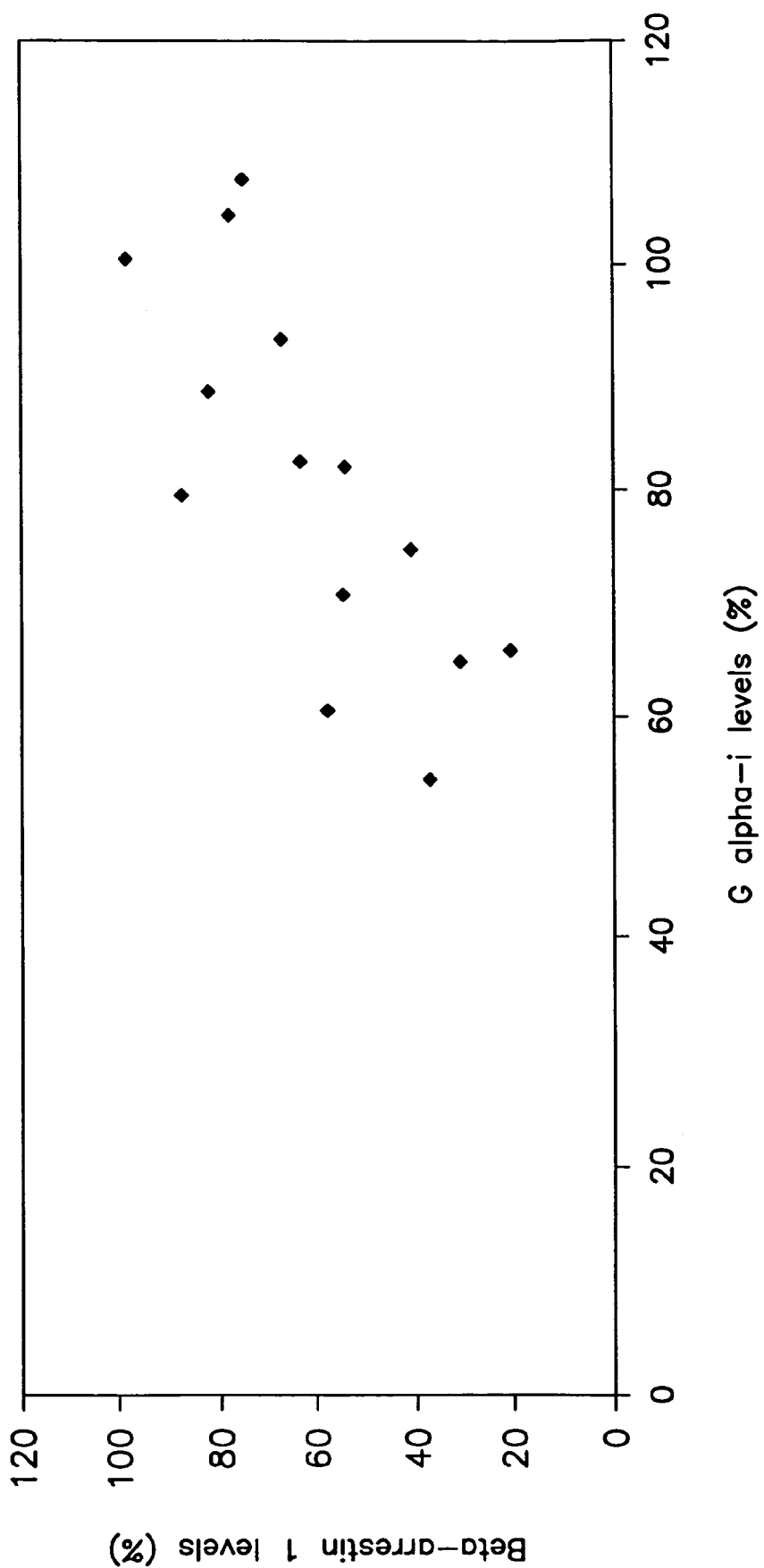
FIG. 8b is a graphical representation of beta-arrestin-1 levels versus G alpha-I levels in patients with depression.

Similar to our previous findings concerning reduced G proteins levels in MNL of patients with depression the patients evaluated for G protein levels in the present study show significant reductions in both G-alpha-s levels (72.0%, SD=11.3%) and G-alpha-i levels (73.2%, SD=12.0%). Cytosolic beta-arrestin-1 levels correlated well with membrane G protein levels measured in the same MNL preparation of the depressed patients (FIGS. 8 A,B). For beta-arrestin-1 versus G-alpha s: Pearson's r=0.635; for beta-arrestin-1 versus G alpha i: Pearson's r=0.751.

Beta-arrestin1 protein and mRNA levels were evaluated in MNL obtained from a group of patients diagnosed with major depressive episode, before the initiation of an antidepressant treatment, during antidepressant treatment at 1, 2 and 4 weeks of treatment and compared with a group of healthy volunteers. As shown by Bonferroni t tests (multiple comparisons against a single control group) in comparison with the age- and gender- matched healthy subjects (cytoplasmic fraction MNL beta-arrestin1 protein=100.0%, SD=6.0%; membrane fraction MNL beta-arrestin1 protein=100.0%, SD=8.7%; MNL mRNA=100.0%, SD=5.9%), patients with depression, while untreated, had statistically significant lower levels of MNL beta-arrestin1 protein (cytoplasmic beta-arrestin-1 protein=45.6%, SD=20.8%, t=9.275, df=65, p<0.001; membrane beta-arrestin-1 protein =37.4%, SD=26.4%, t=8.085, df=65 , p<0.001 ) and significantly lower levels of MNL beta-arrestin-1 mRNA (46.9% SD26.7%, t=5.01, df=65 , p<0.001 ) (Table 5) . The extents of reduction in beta arrestin-1 protein and mRNA levels in untreated patients with depression were found to be correlated with the severity of depressive symptoms assessed by Hamilton Rating Scale for Depression (For cytoplasmic beta-arrestin1 protein: Pearson's r=−0.764, n=14, t=3.93 p<0.005; for membrane beta-arrestin1 protein: Pearson's r=−0.795, n=14, t=4.35 p<0.002; for beta-arrestin1 mRNA levels: Pearson's r=-0.661, t=2.92 n=14, p<0.02).

Figure 9:
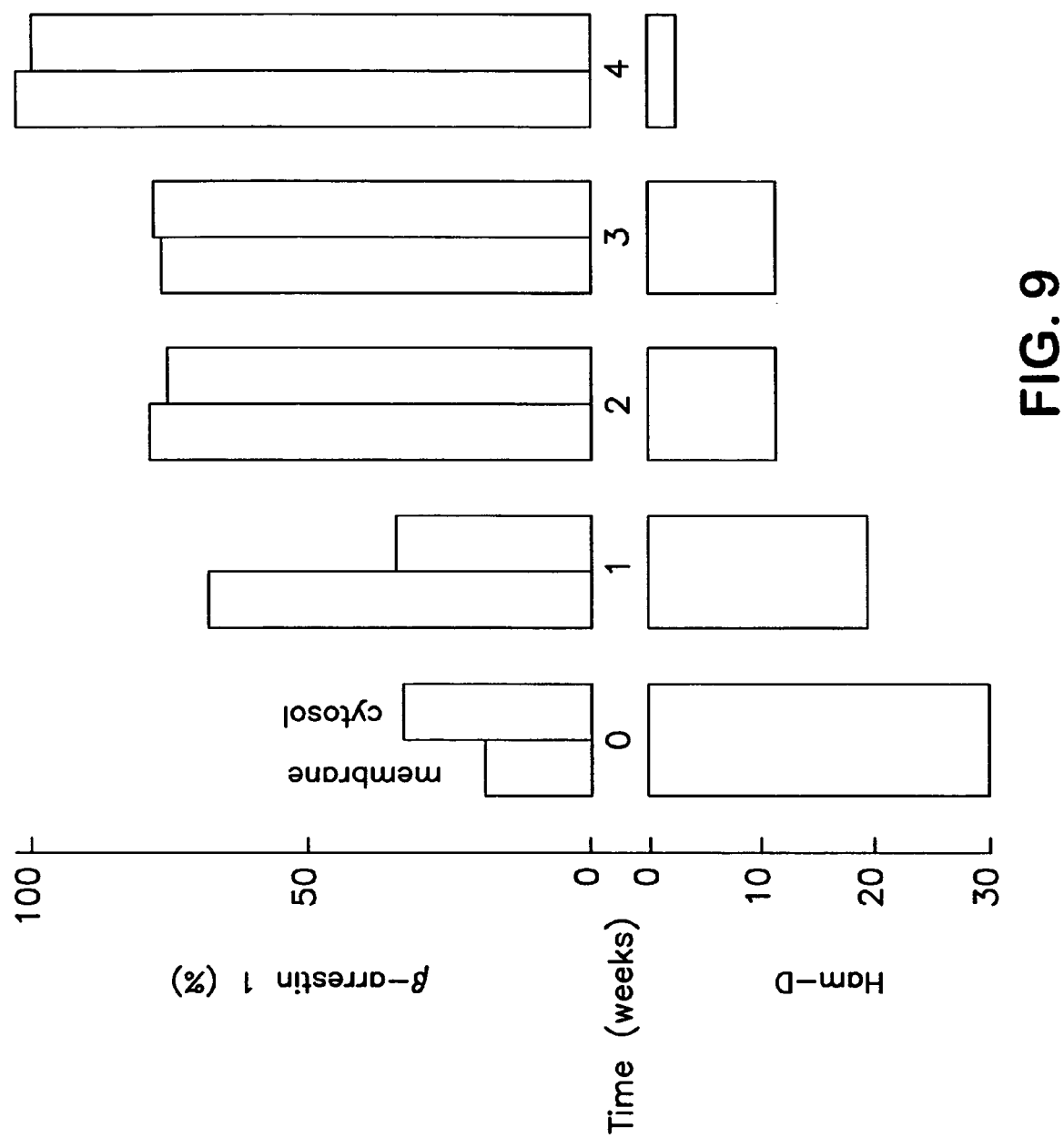
FIG. 9 is a graphical representation of the clinical response of a depressed patient to an antidepressant as well as the representation of the normalization of beta-arrestin-1 levels.

FIG. 9 shows a prototypical example comparing the dynamics of clinical response of a depressed patient to an antidepressant (lowering of the Ham-D rating) with the dynamics of normalization of beta-arrestin levels. Treatment with antidepressant medications resulted in normalization of beta-arrestin1 protein levels in MNL cytoplasmic and membrane fractions and normalization of beta-arrestin1 mRNA levels (Table 5). The low beta-arrestin1 protein and mRNA levels in MNL of the untreated patients with depression were found to be normalized by 4 weeks of antidepressant treatment in a statistically significant manner, according to paired t tests (cytoplasmic MNL beta-arrestin1 protein level 91.7%, SD=21.0%; t=6.956, df=13, p<0.001; membrane MNL beta-arrestin1 protein level 97.2%, SD=18.3%; t=9.203, df=1 3, p<0.001; MNL beta-arrestin1 mRNA level 115.8%, SD=1 0.0%; t=4.925, df=13, p<0.001). Beta-arrestin-1 measures after 4 weeks of antidepressant treatment were found to be not significantly different from those characterizing the group of healthy subjects, according to Bonferroni t test (for cytoplasmic beta-arrestin-1 protein: t=1.010 , df=65, N.S.; for membrane beta-arrestin-1 protein: t=0.135, df=65, N.S.). MNL beta-arrestin1 mRNA levels after 4 weeks of antidepressant treatment were found significantly higher in comparison with levels characterizing healthy volunteers (t=3.15, df=65 , p<0.01).

Figure 10:
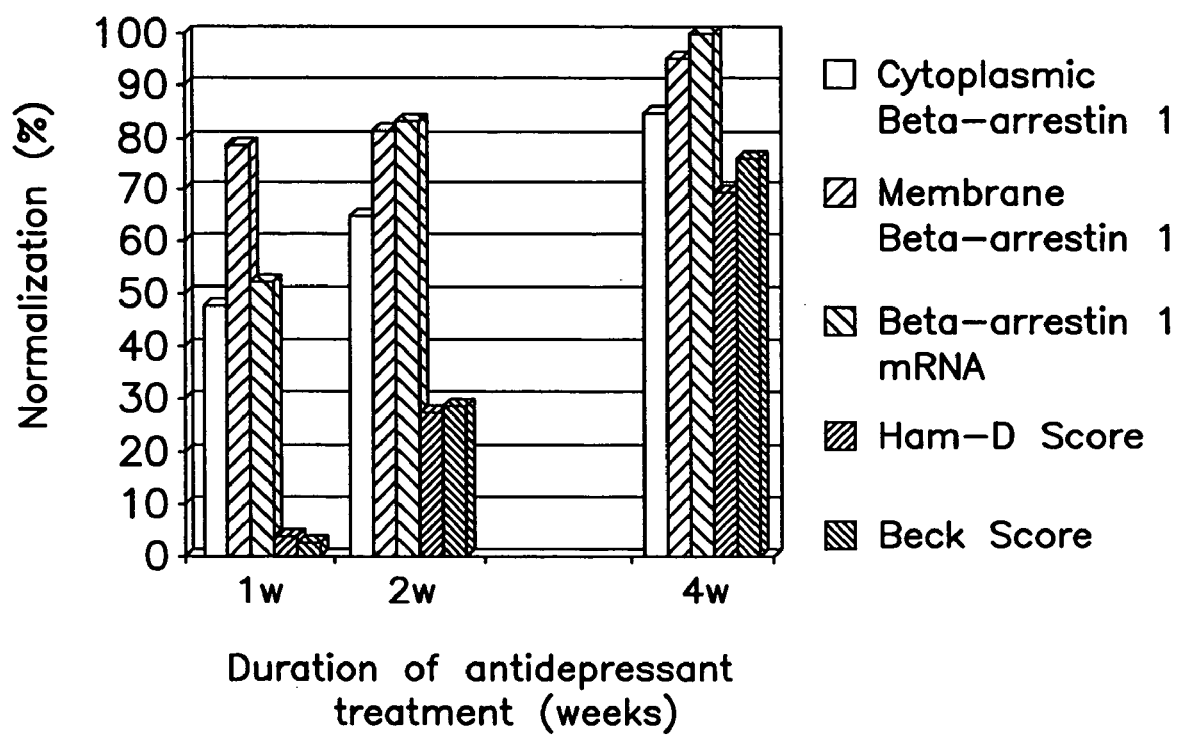
FIG. 10 is a graphical representation of per cent normalization as a function of duration of antidepressant treatment.
Figure 11:
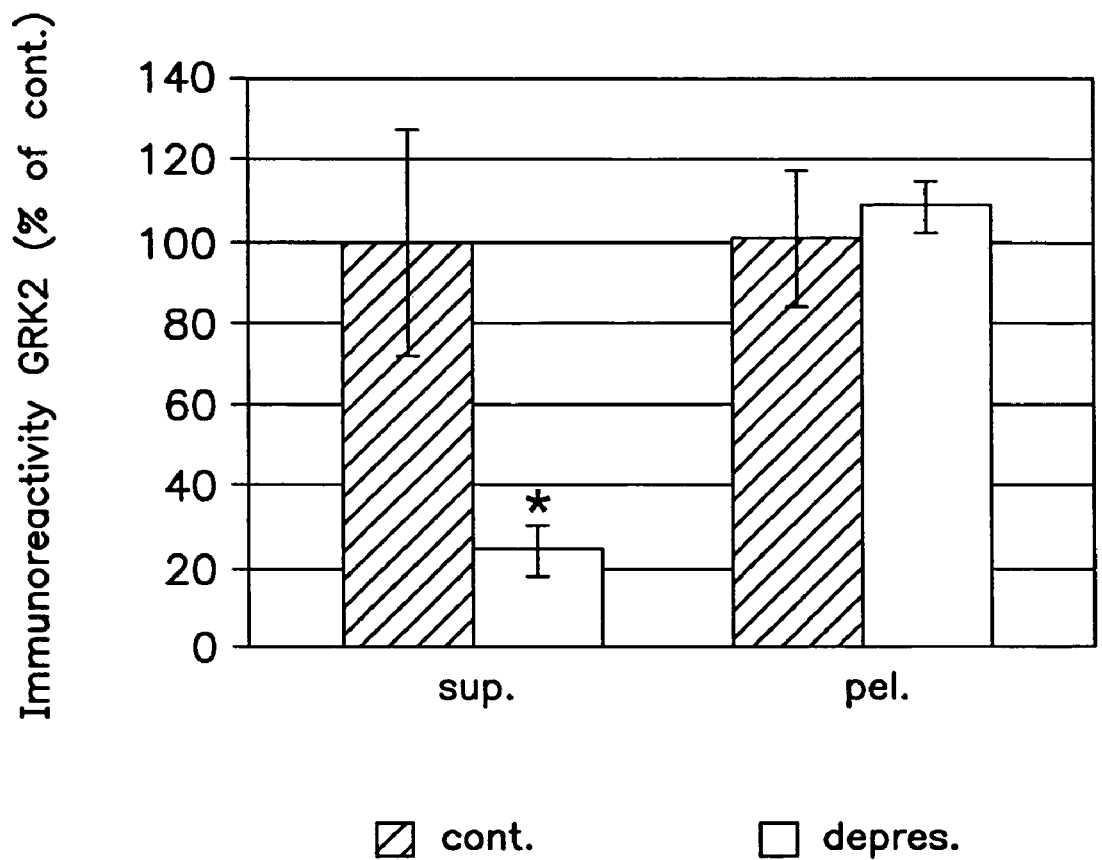
FIG. 11 is a graphical representation of decreased GRK2 levels in the cytolsolic fraction fo MNLs obtained from patients with depression.

Repeated beta-arrestin1 measurements after 1, 2 and 4 weeks of antidepressant treatment conducted alongside with clinical evaluation shows that biochemical normalization of beta-arrestin1 measures preceded clinical response by 1-2 weeks. The detailed dynamics of normalization of the measures of beta-arrestin1 protein and mRNA levels in MNL of the depressed patients during the course of antidepressant treatment in relation to the dynamics of clinical improvement reveals that the biochemical normalization preceded clinical improvement by 1-2 weeks (FIG. 10). The dynamics of biochemical normalization of beta-arrestin1 protein and mRNA levels was not found to significantly differ between the SSRI- and SNRI-treated patients (not shown). While, after 1 week of antidepressant treatment, no significant change was observed in the severity of the depressive symptoms assessed by Hamilton Depression Scale, beta-arrestin1 measures were significantly elevated. The low beta-arrestin1 protein and mRNA levels in MNL of the untreated patients with depression were found to be significantly increased already after one week of antidepressant treatment according to paired t tests (cytoplasmic MNL beta-arrestin1 protein level 71.4%, SD=24.6%; t=3.863, df=13, p<0.002; membrane MNL beta-arrestin1 protein level 86.6%, SD=26.0%; t=6.56, df=13, p<0.001; MNL beta-arrestin1 mRNA level 74.8%, SD=24.5%; t=2.562, df=13, p<0.05).

EXAMPLE 3

GRK and Major Depressive Disorder

The expression of GRK2 was measured in the MNL of 3 patients diagnosed with major depression and compared to 3 healthy subjects. Protein preparations and Western blotting were carried out as described under methods, using a polyclonal antibody. Similarly to the findings in beta-arrestin1 measurements, the immunoreactivity level of GRK2 was significantly decreased (p<0.05, Mann-Whitney Test) in the cytosolic fraction of patients as compared to healthy subjects (FIG. 10). Taken together these data support initial evidence for alterations in signal transduction events in depressed patients, and evidence the involvement of GRK2 and β-arrestin-1 in this process.

From the above Examples, one can see that beta-arrestin-1 is a biochemical underlying target site for the mechanism of action of antidepressants. The induction by antidepressants of the expression of beta-arrestin-1 in rat brain present a defined, general and new mechanism of action of various types of antidepressants: serotonin specific (SSRIs) norepinephrine specific (NSRIs) and non-selective reuptake inhibitors. The elevation in beta-arrestin-1 levels induced by the various types of antidepressants afford a defined and new explanation for their well-known induction of beta-adrenergic and other receptor down-regulation through post-receptor effects.

Reports concerning antidepressants post-receptor effects on G proteins involve proximal effects on receptor-G protein coupling and distal effects on G protein-second messenger activation. In 1983 it was first reported that long-term administration of various antidepressants facilitated the activation of adenylyl cyclase by Gs. These initial findings have been substantiated by later studies. In contrast to the facilitation of G protein-second messenger activation by antidepressants, long-term treatment with these medication was found to decrease beta adrenergic receptor-G protein coupling, as well as 5-HT1A receptor-G protein coupling. These findings of decreased receptor-G protein coupling are consistent with one of the classic biochemical hallmarks of chronic antidepressant treatment: down-regulation of several types of neurotransmitter receptors in the brain. Very recent studies suggest that chronic treatment with antidepressant drugs results in redistribution of Gs, which might partially explain reduced receptor-Gs coupling as well as elevated Gs-adenylyl cyclase coupling.

The present findings describing the induction by antidepressants of beta-arrestin-1 expression offer a new explanation for the mechanism underlying the previously described findings. Increased levels of beta-arrestin-1 'arrest' intracellular signaling triggered by G protein coupled transmembrane receptors. Arrestin binding to receptors thus results in desensitization of G protein-mediated signaling by preventing interaction of receptors with G proteins. Thus proximal antidepressant effects at the level of receptor G protein are expected to show receptor G protein uncoupling due to the increased expression of beta-arrestin-1. Indeed the "proximal" findings on receptor G protein uncoupling support the described above. This receptor G protein uncoupling induced by antidepressants through beta-arrestin-1 induction may be the cause for redistribution of Gs and for the "distal" elevated Gs adenylyl cyclase coupling also described above.

The dynamics of antidepressant-induced increases in the levels of beta-arrestin-1 in rat brain indicate that the process became significant within 10 days and took 2-3 weeks to reach maximal increase.

Also, our findings show that both cytoplasmic and membrane beta-arrestin1 levels are reduced in MNL of patients with depression, suggesting that the protein is under-expressed in depression. Indeed, the reduction in mRNA levels in MNL of patients with depression confirms under-expression of beta-arrestin1 protein in MNL of patients with depression. Similarly, the effects of antidepressants treatment of elevating both cytoplasmic and membrane beta-arrestin1 protein and mRNA levels point to a possible biochemical mechanism of action of antidepressants through increased expression of beta-arrestin1 protein. The time frame of antidepressant induced increase in beta-arrestin-1 levels correlated well with the time frame of antidepressant induced beta-adrenergic and other receptor down-regulation, as well as with the time frame of the clinical response. These findings lend further support to the clinical relevance of the antidepressant effects on the expression of beta-arrestin-1.

The dynamics of normalization by antidepressant treatment of the biochemical measures of beta-arrestin1 levels in MNL of patients with depression did not follow, and thus reflect the clinical improvement of the patients, but rather preceded clinical improvement. The biochemical normalization, which was significant after one week, preceded clinical improvement by 1-2 weeks. It is very difficult to monitor the extent of specific clinical improvement in the early period of the first and second week after initiation of antidepressant treatment. Since clinical response to antidepressant treatments is due both to the specific biochemical antidepressant effects of the medication agent, as well as placebo effects, and since the placebo effect is usually more pronounced during the early period of treatment initiation, it is very difficult to assess in these early days the specific antidepressant effects of antidepressant treatments. Beta-arrestin1 measurements in peripheral blood cells of patients with mood disorder, as a state dependent characteristic, may afford biochemical monitoring of antidepressant effects and prediction of clinical response to antidepressant by 1-2 weeks in advance.

Comparing between the findings of reduced beta-arrestin-1 levels with simultaneous findings of reduced G alpha-s and G alpha-i levels in MNL of patients with depression it is clear that the extend of reduction was found to be more prominent by two to three folds, with respect to beta-arrestin levels. While beta-arrestin-1 levels were reduced by 62.9%, G alpha-s and G alpha-i protein levels were reduced by 28% and 27%, respectively, in unipolar outpatients with depression in the present study. Similar extent of reductions of G protein levels were observed by us in previous studies: reductions of G-alpha-s and G-alpha-i by 21% and 23%, respectively in unipolar depressed patients; by 29% and 39%, respectively in hospitalised depressed patients before the application of ECT in a previous study; by 28% and 20%, respectively in SAD outpatients with winter depression and by 21% and 17%, respectively for bipolar depressed patients (Table 4).

Thus, it can be concluded that beta-arrestin-1 measurements in MNL of patients with depression is a better diagnostic assay for detecting depression. Indeed the sensitivity and specificity of the beta-arrestin-1 test were found to be 92.5% and 93.9%, respectively. These values are far greater than the values previously described for the immunoreactive G protein assay: 73% and 81%, respectively.

From the results documented in the above examples it will be realized that the present invention, inter alia enables and provides for:

(i) A new target for the mechanism of action of antidepressant drugs acting on beta-arrestin and/or GRK2 levels and/or functioning and the ability to design new antidepressant medication through this mechanism of action, using similar techniques of measurements in animal brain and human peripheral models.

(ii) The use of genetic polymorphism at the beta-arrestin 1 or GRK-2 locci in the pharmacogenetics of molecular predictions of response to treatment in mood disorders.

(iii) The possibility to diagnose major depressive episode in a yet untreated subject using the beta-arrestin-1 and/or GRK2 assay, which has proven far better sensitivity and specificity than the previous G protein assays.

(iv) The possibility to monitor and/or predicting treatment response or treatment resistance to antidepressant medications.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

References:

Avissar S, Schreiber G: Towards molecular diagnostics of mood disorders in psychiatry. TRENDS in Molecular Medicine. 8:294-300, 2002.

Schreiber G, Avissar S: Application of G proteins in the molecular diagnosis of psychiatric disorders. Expert Rev Mol Diagn. 3:89-100, 2003.

What is claimed is:

1. A method for gauging the effect of a depression treatment upon a patient suffering from depression, comprising:
determining the level of a beta-arrestin 1 present in mononuclear leukocytes from blood in a patient before and after treatment of said patient for depression; and
comparing said levels,
wherein an increase in said level of beta-arrestin 1 is indicative of a positive effect of the treatment.

2. The method according to claim 1, wherein the treatment comprises administration of a serotonin specific reuptake inhibitor.

3. The method according to claim 1, wherein the treatment comprises administration of a norepinephrine specific reuptake inhibitor.

4. The method according to claim 1, wherein the treatment comprises administration of a non-selective reuptake inhibitor.

5. The method according to claim 1, further comprising:
determining the level of a G-protein coupled receptor kinase 2 in mononuclear leukocytes obtained from a patient during treatment; and
comparing said level to that obtained from mononuclear leukocytes of a patient before treatment.

6. The method according to claim 5, wherein the treatment comprises administration of a serotonin specific reuptake inhibitor.

7. The method according to claim 5, wherein the treatment comprises administration of a norepinephrine specific reuptake inhibitor.

8. The method according to claim 5, wherein the treatment comprises administration of a non-selective reuptake inhibitor.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: synthetic beta-actin forward primer

<400> SEQUENCE: 1
ctacaatgag ctgcgtgtgg                                              20

<210> SEQ ID NO 2
<211> LENGTH: 18
<212> TYPE: DNA
<213> ORGANISM: Artificial Sequence
<220> FEATURE:
<223> OTHER INFORMATION: synthetic beta-actin reverse primer

<400> SEQUENCE: 2
cggtgaggat cttcatga                                                18

<210> SEQ ID NO 3
<211> LENGTH: 20
<212> TYPE: DNA
```

```
<213> ORGANISM: Artificial Sequence
<220> FEATURE:
<223> OTHER INFORMATION: synthetic beta-arrestin1 forward primer

<400> SEQUENCE: 3
caagcccttg cacctagaag                                            20

<210> SEQ ID NO 4
<211> LENGTH: 20
<212> TYPE: DNA
<213> ORGANISM: Artificial Sequence
<220> FEATURE:
<223> OTHER INFORMATION: synthetic beta-arrestin1 reverse primer

<400> SEQUENCE: 4
gttcgtgtct tcgtgcttga                                            20
```